United States Patent [19]

Ciaudelli et al.

[11] Patent Number: 4,567,038

[45] Date of Patent: Jan. 28, 1986

[54] SUNSCREEN COMPOSITION FOR HAIR PROTECTION

[75] Inventors: Joseph P. Ciaudelli, Ramsey, N.J.; Elizabeth Brand, New York, N.Y.

[73] Assignee: Revlon, Inc., New York, N.Y.

[21] Appl. No.: 708,780

[22] Filed: Mar. 6, 1985

[51] Int. Cl.$^4$ .......................... A61K 7/08; A61K 7/09; A61K 7/42

[52] U.S. Cl. ........................................ 424/59; 424/60; 424/70; 424/71; 424/72; 514/880; 514/881

[58] Field of Search .............................. 424/59, 60, 70

[56] References Cited

U.S. PATENT DOCUMENTS 4,445,521  5/1984  Grollier et al. ........................ 424/70

FOREIGN PATENT DOCUMENTS

| 662111 | 8/1965 | Belgium | 424/70 |
| 2003487 | 8/1970 | Fed. Rep. of Germany | 424/70 |
| T2706503 | 8/1978 | Fed. Rep. of Germany | 424/70 |
| 0088408 | 5/1984 | Japan | 424/70 |
| 0088409 | 5/1984 | Japan | 424/70 |
| 0108709 | 6/1984 | Japan | 424/70 |
| 7604794 | 11/1976 | Netherlands | 424/70 |

OTHER PUBLICATIONS

Chemical Abstracts, 1966, vol. 65, p. 3665 (equivalent to 662,111 (Belgium Patent)).

Kass, Cosmetics & Toiletries, 3/1976, vol. 91, pp. 87 to 94.

*Primary Examiner*—Dale R. Ore

[57] ABSTRACT

A sunscreen composition for application to hair is provided comprising a mousse base or concentrate containing a sunscreen agent therein, said mousse base or concentrate comprising a cationic surfactant substantive to hair and a nonionic film-former which in combination with a nonionic surfactant produces foam in the composition and upon application to hair forms a coating thereon.

6 Claims, No Drawings

SUNSCREEN COMPOSITION FOR HAIR PROTECTION

BACKGROUND OF THE INVENTION

1. Field of the Invention

This invention relates to new cosmetic compositions for the protection of the hair from the bleaching effect of sunlight and more particularly to sunscreen mousse products for use in protecting the hair from bleaching by sunlight.

2. Description of the Prior Art

Radiation of light having wavelengths ranging from 2950 A. to 4000 A. produces pigmentation or tanning on the human skin. Light of wavelengths ranging from 2950 A. to 3150 A. of sufficient intensity produces erythema, while light of wavelengths from 3150 A. to 4000 A. produces an apparent direct tanning after exposure of sufficient duration and intensity without an accompanying erythema.

The prior art utilizes sunscreen agents, applied to the skin in suitable formulations, to provide protection against erythema causing radiation and to provide the desired degree of tanning with safety. Sunscreen formulations are generally tailor-made to possess sun protective factors (SPF) ranging from 2 to 15 to provide for various degrees of protection and tanning. The agents used in sunscreen formulations include para-aminobenzoates, benzophenones, cinnamates, salicylates, gallates and mixtures thereof.

Radiation of light having wavelengths ranging from 2950 A. to 4000 A. not only affects the skin but also the hair and may result in physical and chemical changes such as weakened, dry and brittle hair structure. The most apparent of these changes is the "bleached" appearance of the hair after exposure to intense sunlight especially during the summer months.

Hair treatment products in the form of shampoos, conditioners, rinses, setting lotions, permanent wave agents and the like do not provide protection against damage caused by radiation and especially against the bleaching effect.

The present invention addresses this problem by providing sunscreen mousse products which, when applied to the hair, substantially block or reduce the amount of radiation reaching the hair and thereby inhibit the bleaching thereof.

SUMMARY OF THE INVENTION

Consistent with this object, and others which will become apparent from the description of the invention, a composition is provided consisting of a mousse base or concentrate containing therein at least a sunscreening agent.

The mousse base or concentrate generally comprises a cationic surfactant which is substantive to the hair by virtue of electrostatic attraction and a nonionic resin which is a film-former polymer to coat and thereby provide holding effect to the hair.

The sunscreen agents used in the composition of the present invention must be compatible with the mousse-base or concentrate, i.e. must be at least water miscible and preferably water soluble. In addition, the sunscreen agents should not affect the ideal white color of the foam and consistency of the mousse base or concentrate.

DETAILED DESCRIPTION OF THE INVENTION

The composition of the present invention, in the form of a generally white foam contained in a pressurized container, is useful for conditioning the hair while at the same time protecting the hair from the harmful rays of the sun which tend to weaken, break and bleach the hair. The composition may be used on dry as well as wet hair which has been shampood or cleaned or at any time when a "wet look" or custom styling of the hair is desired.

The general formula for compositions of the present invention is as follows:

| Ingredients | % w/w |
| --- | --- |
| Sunscreen agent | 0.001–15.0 |
| Alcohol | 2.0–15.0 |
| Nonionic resin/film-former | 0.5–10.0 |
| Nonionic surfactant/emulsifier/foam producer | 0.1–2.0 |
| Fragrance | 0.01–0.2 |
| Protein conditioner | 0.01–0.5 |
| Water soluble silicone | 0.1–0.8 |
| Cationic surfactant | 0.1–5.0 |
| Acid to maintain pH at 4.5–6.5 | 0.001–1.0 |
| Nonionic surfactant/stabilizer | 0.1–1.0 |
| Water qs. to | 100 |

A preferred composition of the present invention is shown in Example 1.

EXAMPLE 1

| Ingredients | % w/w |
| --- | --- |
| 2 parts Lusantan-25/1 part Parsol Hydro (Ethoxylated p-amino benzoate/diethanol amine salt of p-methoxycinnamic acid) | 13.8 |
| SDA 40 (Ethyl alcohol) | 5.0 |
| PVP/VAE735 (Copolymer of vinyl acetate and vinyl pyrrolidone) | 2.0 |
| Oleth-20 (Polyethylene glycol ether of oleyl alcohol-20 ethylene glycol units) | 0.5 |
| Fragrance | 0.1 |
| Hydrolyzed animal protein | 0.01 |
| Dimethicone copolyol (Polymer of dimethylsiloxane with polyoxyethylene and/or polyoxypropylene side chain) | 0.15 |
| Quat 26 (Mink amido propyl dimethyl 2-hydroxy ammonium chloride - Van Dyk's Ceraphyl 65) | 0.25 |
| Citric Acid pH 4.5–5.5 | 0.008 |
| Octoxynol 9 (Ethoxylated octylphenol-TritonX-100, Rohm & Haas) | 0.2 |
| Water qs to | 100 |

Sunscreening agents normally used to absorb sunlight are oil miscible and water immiscible. The sunscreen agent of the present invention must be water miscible and preferably water soluble. Water soluble sunscreen agents of the present invention include: ethoxylated p-amino benzoate (Peg-25 PABA, sold by BASF), diethanol amine salt of p-methoxycinnamic acid (Parsol Hydro sold by Givaudan Corp.), 2-hydroxy-4-methoxybenzophenone-5-sulfonic acid and disodium 2,2'-dihydroxy- 4-4'-dimethoxy-5-5'-disulfobenzophenone, p-demethylamino benzoic acid dimethylamino propyl amine salt, p-dimethylamino benzoic acid diethanol amine salt, and trimethyl-2-hydroxy propyl-p-dimethylamino benzoate ammonium chloride.

Other sunscreen agents used in the present invention are those soluble in alcohols and compatible with water, such as 2,4-dihydroxybenzophenone, 2-hydroxy-4-methoxybenzo- phenone, 2,2',4,4'-tetrahydroxybenzophenone and 2,2'-dihydroxy- 4,4'-dimethoxybenzophenone.

While the concentration of a sunscreen agent or a mixture of sunscreen agents according to the present invention may be as high as 15% w/w, we prefer to use a concentration from about 0.001% to about 0.5% and more preferably from about 0.001% to 0.1%. The reason for this preference is that some sunscreen agents at or about 0.5w/w or higher may impart an esthetically undesirable color to the mousse formulation.

The preferred alcohol used in the practice of the present invention is ethanol, however, the use of other low molecular weight alcohols is also contemplated, such as n-propanol and iso-propanol.

The preferred nonionic polymer which upon application of the mousse formulation forms a film coating on the hair is a copolymer of vinyl acetate and vinyl pyrrolidone, sold as a liquid in 50% ethanol as PVP/VA-E735. This nonionic polymer used together with a nonionic surfactant, acting as an emulsifier, such as Oleth 20 (polyethylene glycol ether of Oleyl Alcohol that conforms to the formula $CH_3(CH_2)_7CH=CH(CH_2)_7CH_2(OCH_2CH_2)_nOH$, where n has an average value of 20) produces the desired foam consistency and degree of hold characteristic of mousse formulations.

In addition to Oleth 20, other nonionic surfactants may be used, such as: Oleth 10 (polyethylene glycol ether of Oleyl Alcohol that conforms to the formula $CH_3(CH_2)_7CH=CH(CH_2)_7CH_2(OCH_2CH_2)_nOH$ where n has an average value of 10); Steareth 20 (polyethylene glycol ether of Stearyl Alcohol that conforms to the formula $CH_3(CH_2)_{16}CH_2(OCH_2CH_2)_nOH$ where n has an average value of 2); Steareth 20 (polyethylene glycol ether of Stearyl Alcohol that conforms to the formula $CH_3(CH_2)_{16}CH_2(OCH_2CH_2)_nOH$ where n has an average value of 20); Polysorbate 20 (mixture of laurate esters of sorbitol and sorbitol anhydrides, conforming generally to the formula

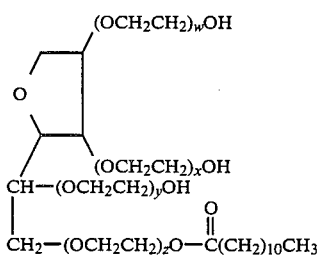

where w + x + y + z has an average value of 20); and Polysorbate 80 (mixture of oleate esters of sorbitol and sorbitol anhydrides, conforming generally to the formula

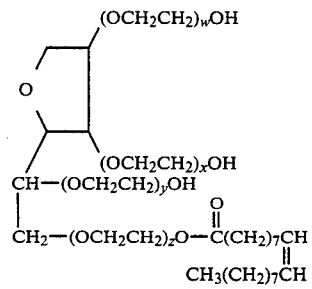

where w + x + y + z has an average value of 20).

As a plasticizer, we prefer to use Dimethicone copolyol (a polymer of dimethylsiloxane with polyoxyethylene and/or polyoxypropylene side chains) sold under various trade names, such as Dow Corning 193 Surfactant (Dow Corning) and Silicone L-720 (Union Carbide). However, other water soluble silicone plasticizers may also be used as well.

A cationic salt which is substantive to the hair by electrostatic attraction is used in the formulations of the present invention. Quaternium-26 (Minkamidopropyl dimethyl 2-hydroxy-ethyl ammonium chloride) is preferred, however other cationic salts, such as Quaternium-24 (Decyl dimethyl octyl ammonium chloride) or Quaternium-30 (Isododecylbenzyl triethanolammonium chloride) may also be used.

The nonionic surfactant Octoxynol-9 ($C_8H_{17}C_6H_4(OCH_2CH_2)_nOH$ where n has an average value of 9) is used as a stabilizer in the present invention. In its place, or in admixture therewith other nonionic surfactants may also be used, such as Octoxynol-7 (Polyethylene glycol (7) octyl phenyl ether that conforms generally to the formula $C_8H_{17}C_8H_4(OCH_2CH_2)_nOH$ where n has an average value of 7) and Octoxynol-10 (Polyoxyethylene (10) octyl phenyl ether that conforms generally to the formula $C_8H_{17}C_6H_4(OCH_2CH_2)_nOH$ where n has an average value of 10).

To provide for the desired foam properties, the pH should be maintained at about 4.5 to 6.5 and preferably at 4.5 to 5.5.

The following non-limiting examples illustrate the compositions of the present invention.

EXAMPLE 2

| Ingredients | % w/w |
| --- | --- |
| Hydroxyethyl cellulose | 0.225 |
| Benzophenone-9 | 0.001 |
| Hyd. animal protein | 0.010 |
| Steareth-2 | 0.500 |
| Dimethicone copolyol | 0.300 |
| Nonoxynol-10 | 0.150 |
| Polysorbate-20 | 0.638 |
| Polyquat-11 | 2.000 |
| SDA 40B | 3.000 |
| Tallowtrimonium Cl | 0.500 |
| Polyquaternium-4 | 0.050 |
| Benzophenone-2 | 0.001 |
| PVP/VA Copolymer | 6.750 |
| Water q.s. | 100 |

EXAMPLE 3

| Ingredients | % w/w |
|---|---|
| Hydroxyethyl cellulose | 0.300 |
| Ammonium hydroxide | 0.050 |
| Benzophenone-9 | 0.001 |
| Hydrolyzed animal protein | 0.010 |
| Nonoxynol-10 | 0.150 |
| Dimethicone copolyol | 0.300 |
| Trimethyl tallow ammonium chloride | 0.500 |
| Polyquaternium 11 | 2.000 |
| Polysorbate-20 | 0.638 |
| Citric acid | 0.050 |
| Palmitoyldimonium hyd. animal collagen | 0.300 |
| SDA alcohol 40B | 3.000 |
| Benzophenone-2 | 0.001 |
| Sorbitan sesquioleate | 0.362 |
| PVP/VA copolymer (50% in alcohol) | 3.000 |
| Fragrance | 0.200 |
| Water q.s. | 100 |

EXAMPLE 4

| Ingredient | % w/w |
|---|---|
| Hydroxyethyl cellulose | 0.300 |
| NH$_4$OH | 0.030 |
| Benzophenone-9 | 0.050 |
| Hydrolyzed animal protein | 0.010 |
| Nonoxynol-10 | 0.150 |
| Dimethicone copolyol | 0.300 |
| Tallowtrimonium chloride | 0.500 |
| Polyquaternium-11 | 2.000 |
| Polysorbate-20 | 0.638 |
| Citric acid | 0.040 |
| SDA 40B | 3.000 |
| Benzophenone-2 | 0.050 |
| PVP/VA copolymer | 5.000 |
| Water q.s. | 100 |

EXAMPLES 5–8

| Ingredients | 5 % w/w | 6 % w/w | 7 % w/w | 8 % w/w |
|---|---|---|---|---|
| Hydroxyethyl cellulose | 0.150 | 0.150 | 0.150 | 0.150 |
| NH$_4$OH | q.s. | q.s. | q.s. | q.s. |
| Benzophenone-9 | 0.001 | 0.001 | 0.001 | 0.001 |
| Hyd. animal protein | 0.010 | 0.010 | 0.010 | 0.010 |
| Nonoxynol-10 | 0.150 | 0.150 | 0.150 | 0.150 |
| Dimethicone copolyol | 0.200 | 0.200 | 0.200 | 0.000 |
| Polyquat-11 | 2.000 | 2.000 | 2.000 | 2.000 |
| Polysorbate-20 | 0.200 | 0.600 | 0.600 | 0.600 |
| Tallowtrimonium Cl | 0.400 | 0.400 | 0.400 | 0.400 |
| Polyquat-4 | 0.200 | 0.200 | 0.200 | 0.200 |
| Citric acid | q.s. | q.s. | q.s. | q.s. |
| SDA 40B | 3.000 | 3.000 | 3.000 | 3.000 |
| Benzophenone-2 | 0.001 | 0.001 | 0.001 | 0.001 |
| PVP/VA E-735 | 6.750 | 6.750 | 6.750 | 6.750 |
| Sorbitan sesquioleate | 0.200 | 0.400 | 0.400 | 0.400 |
| Laureth-4 | 0.250 | 0.000 | 0.000 | 0.000 |
| Steareth-2 | 0.000 | 0.000 | 0.200 | 0.000 |
| Water | q.s. 100 | q.s. 100 | q.s. 100 | q.s. 100 |

EXAMPLES 9–13

| Ingredients | 9 % w/w | 10 % w/w | 11 % w/w | 12 % w/w | 13 % w/w |
|---|---|---|---|---|---|
| Hydroxyethyl cellulose | 0.150 | 0.300 | 0.300 | 0.300 | 0.300 |
| NH$_4$OH | q.s. | 0.030 | 0.030 | 0.030 | 0.030 |
| Benzophenone-9 | 0.001 | 0.001 | 0.001 | 0.001 | 0.001 |
| Hyd. animal protein | 0.010 | 0.010 | 0.010 | 0.010 | 0.010 |
| Dimethicone copolyol | 0.200 | 0.300 | 0.300 | 0.300 | 0.300 |
| Polyquat-11 | 2.000 | 2.000 | 2.000 | 2.000 | 2.000 |
| Polysorbate-20 | 0.200 | 0.638 | 0.638 | 0.638 | 0.638 |
| Polyquat-4 | 0.050 | 0.050 | 0.050 | 0.050 | 0.050 |
| Citric acid | q.s. | 0.040 | 0.040 | 0.040 | 0.040 |
| Nonoxynol-10 | 0.150 | 0.150 | 0.150 | 0.150 | 0.150 |
| SDA 40B | 3.000 | 3.000 | 3.000 | 3.000 | 3.000 |
| Benzophenone-2 | 0.001 | 0.001 | 0.001 | 0.001 | 0.001 |
| PVP/VA E735 | 6.750 | 6.750 | 6.750 | 6.750 | 6.750 |
| Sorbitan sesquioleate | 0.400 | 0.362 | 0.000 | 0.000 | 0.050 |
| Steareth-2 | 0.000 | 0.000 | 0.362 | 0.200 | 0.362 |
| Water | q.s. 100 | q.s. 100 | q.s. 100 | q.s. 100 | q.s. 100 |

EXAMPLES 14–17

| Ingredients | 14 % w/w | 15 % w/w | 16 % w/w | 17 % w/w |
|---|---|---|---|---|
| Hydroxyethyl cellulose | 0.150 | 0.150 | 0.150 | 0.150 |
| NH$_4$OH | q.s. | q.s. | q.s. | q.s. |
| Benzophenone-9 | 0.001 | 0.001 | 0.001 | 0.001 |
| Hyd. animal protein | 0.010 | 0.010 | 0.010 | 0.010 |
| Nonoxynol-10 | 0.150 | 0.150 | 0.150 | 0.150 |
| Dimethicone copolyol | 0.200 | 0.200 | 0.200 | 0.200 |
| Polyquat-11 | 2.000 | 2.000 | 2.000 | 2.000 |
| Polysorbate-20 | 0.000 | 0.600 | 0.600 | 0.200 |
| Tallowtrimonium Cl | 0.400 | 0.400 | 0.400 | 0.400 |
| Polyquat-4 | 0.200 | 0.200 | 0.200 | 0.200 |
| Citric acid | 0.020 | 0.020 | 0.020 | 0.020 |
| Steareth-20 | 0.850 | 0.000 | 0.000 | 0.000 |
| Polysorbate 85/Tween 185 | 0.000 | 0.000 | 0.000 | 0.200 |
| SDA 40B | 3.000 | 3.000 | 3.000 | 3.000 |
| Benzophenone-2 | 0.001 | 0.001 | 0.001 | 0.001 |
| PVP/VA E735 | 6.750 | 6.750 | 6.750 | 6.750 |
| Sorbitan sesquioleate | 0.000 | 0.000 | 0.200 | 0.200 |
| Steareth-2 | 0.150 | 0.000 | 0.000 | 0.000 |
| Sorbitan monolaurate | 0.000 | 0.200 | 0.200 | 0.000 |
| Water | q.s. 100 | q.s. 100 | q.s. 100 | q.s. 100 |

A preferred method of preparing sunscreen compositions of the present invention follows. Ingredients used in this method correspond to ingredients used in Example 2.

Mixture A

50–70 parts of cold water is charged into a manufacturing kettle equipped with variable speed propeller-type or counter rotation/side scraper-type agitation means. While the water is being agitated, the formula amount of hydroxyethyl cellulose is added and agitation continues until complete dispertion is obtained. Next, Benzophenone-9, Hydrolyzed animal protein, Steareth-2 and Dimethicone copolyol are added into the kettle while heating the mixture to 60°–65°C. Heating at 60°–65°C. and agitation continue for at least 30 minutes so that the mixture is uniform and free of lumps. The mixture is next cooled to 40°–45°C., followed by the addition of Nonoxynol-10, Polysorbate-20 and Polyquat-11. Slow agitation is maintained while the mixture is cooled to 30°–35°C.

Mixture B

Into a suitable size side tank are charged the formula amounts of special denatured alcohol, tallowtrimonium chloride, Benzophenone-2 and PVP/VA copolymer and mixed until the ingredients are dissolved.

Mixture B is transferred into manufacturing kettle containing Mixture A while maintaining continuous slow agitation. The side tank is then rinsed with water sufficient to make the formula amount and the rinsing is charged into the kettle. The mixture is mixed for at least 30 minutes until uniform bulk is obtained. The pH is checked and, if necessary, is adjusted with citric acid or ammonium hydroxide.

The sunscreen composition is filled into cans and the cans pressurized with propellants using conventional, state of the art techniques.

Formulations of the present inventions were tested on human hair by applying the same thereto using methods conventional with mousse applications. The formulations were found effective both with respect to sunscreen properties and conditioning qualities characteristic of mousse formulations.

The present invention has been described with respect to the preferred embodiments of the invention. It will be clear to those skilled in the art that modifications and or variations of the disclosed compositions may be made without departing from the scope of the invention set forth herein.

What is claimed is:

1. A sunscreen mousse composition comprising by weight:
   0.001% to 15% of at least one sunscreen agent selected from the group consisting of ethoxylated p-amino benzoate, a diethanol amine salt of p-methoxycinnamic acid, 2-hydroxy-4-methoxybenzophenone-5-sulfonic acid, disodium 2,2'-dihydroxy-4-4'-dimethoxy-5-5'-disulfobenzophenone, 2,4-dihydroxy-benzophenone, 2-hydroxy-4-methoxybenzophenone, 2,2',4,4'-tetrahydroxybenzophenone, 2,2'-dihydroxy-4,4'-dimethoxy-benzophenone, a dimethylamino propyl amine salt of p-dimethylamino-benzoic acid, a diethanolamine salt of p-dimethylamino benzoic acid, and trimethyl-2-hydroxy propyl-p-dimethylamino benzoate ammonium chloride;
   2.0 to 15.0% of an alcohol;
   0.5% to 10.0% of a nonionic film-former;
   0.1% to 2.0% of a nonionic surfactant selected from the group consisting of polythylene glycol ether of oleyl alcohol having the formula $CH_3(CH_2)_7CH=CH(CH_2)(OCH_2CH_2)_nOH$ wherein n has an average value of 20, polyethylene glycol ether of oleyl alcohol having the formula $CH_3(CH_2)_7CH=CH(CH_2)_7CH_2(OCH_2CH_2)_nOH$ wherein n has an average value of 10, polyethylene glycol ether of stearyl alcohol having the formula $CH_3(CH_2)_{16}CH_2(OCH_2)_nOH$ wherein n has an average value of 2, polyethylene glycol ether of stearyl alcohol having the formula $CH_3(CH_2)_{16}CH_2(OCH_2CH_2)_nOH$ wherein n has an average value of 20;

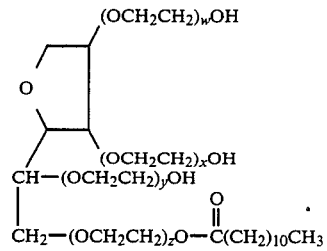

where $w + x + y + z$ has an average value of 20; and

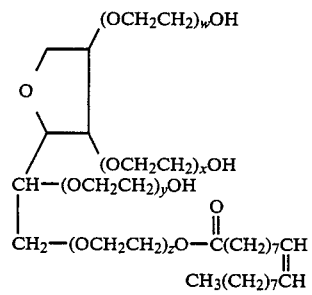

where $w + x + y + z$ has an average value of 20;
   0.01–0.5% of a protein conditioner
   0.1% to 0.8% of the water soluble plasticizer dimethylsiloxane with polyoxyethylene and/or polyoxypropylene side chains;
   0.1% to 5.0% of a cationic surfactant selected from the group consisting of minkamidopropyl dimethyl 2-hydroxy-ethyl ammonium chloride, decyl dimethyl octyl ammonium chloride and isododecylbenzyl triethanolammonium chloride; and
   q.s. 100% water.

2. The sunscreen mousse composition of claim 1 further comprising a nonionic surfactant/stabilizer.

3. The sunscreen mousse composition of claim 1 wherein said cosmetically acceptable alcohol is ethanol.

4. The sunscreen mousse composition of claim 1 wherein said nonionic film-former is a copolymer of vinyl acetate and vinyl pyrrolidone.

5. The sunscreen mousse composition of claim 1 wherein said sunscreen agent is present in a concentration of 0.001% to 0.5.

6. The sunscreen mousse composition of claim 1 having a pH of 4.5 to 5.5.

* * * * *